(12) United States Patent
Hernandez Rivera et al.

(10) Patent No.: US 10,379,033 B1
(45) Date of Patent: Aug. 13, 2019

(54) COUPLING OF THIN LAYER CHROMATOGRAPHY (TLC) TO QUANTUM CASCADE LASER SPECTROSCOPY (QCLS) FOR QUALITATIVE AND QUANTITATIVE FIELD ANALYSES OF EXPLOSIVES AND OTHER POLLUTANTS

(71) Applicants: Samuel P. Hernandez Rivera, Mayaguez, PR (US); John R. Castro Suarez, Mayaguez, PR (US)

(72) Inventors: Samuel P. Hernandez Rivera, Mayaguez, PR (US); John R. Castro Suarez, Mayaguez, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 15/615,774

(22) Filed: Jun. 6, 2017

Related U.S. Application Data

(60) Provisional application No. 62/346,145, filed on Jun. 6, 2016.

(51) Int. Cl.
*G01N 21/27* (2006.01)
*G01N 21/25* (2006.01)
*G01N 21/47* (2006.01)

(52) U.S. Cl.
CPC ........... *G01N 21/255* (2013.01); *G01N 21/27* (2013.01); *G01N 21/4738* (2013.01); *G01N 2201/1293* (2013.01)

(58) Field of Classification Search
CPC ........ G01N 21/27; G01N 21/47; G01N 21/59; G01N 21/64; G01N 21/255; G01N 21/643;
(Continued)

(56) References Cited

U.S. PATENT DOCUMENTS

| 2012/0033220 A1* | 2/2012 | Kotidis | B82Y 20/00 356/445 |
| 2012/0282705 A1* | 11/2012 | Lei | G01N 21/643 436/110 |
| 2013/0199982 A1* | 8/2013 | Linford | B01J 20/3297 210/198.3 |

\* cited by examiner

*Primary Examiner* — Jamil Ahmed
(74) *Attorney, Agent, or Firm* — Hoglund & Pamias, PSC; Roberto J. Rios

(57) ABSTRACT

The invention provides the use of instrumentation and methods for the rapid separation, detection, and identification of chemical compounds by coupling a well-established chromatographic separation science technique, TLC, with mid-infrared (MIR) QCLS for the analysis of explosives, pollutants, and other threat chemicals. The stationary phases were silica gel adhered to metallic aluminum supports. The mobile phases consisted of organic solvents and their mixes. The position and spot diameter of the TNT samples on the plate containing the adsorbent silica film were measured and compared before and after the chromatographic runs. The MIR vibrational identification of TNT was performed through reflectance measurements using a widely tunable three-diode source. The symmetric stretching vibration of the nitro group $[v_s(NO_2)]$ centered at approximately 1350 $cm^{-1}$ and the asymmetric stretching vibration of the nitro group $[v_{as}(NO_2)]$ at approximately 1530 $cm^{-1}$ were clearly observed. TLC-QCLS allows for the rapid and reproducible separation, identification, and quantification of explosives in the field in a short amount of time.

10 Claims, 4 Drawing Sheets
(4 of 4 Drawing Sheet(s) Filed in Color)

(58) Field of Classification Search
CPC ......... G01N 21/4738; G01N 2201/1293; B01J 20/3297; B82Y 20/00; B82Y 40/00; B82Y 30/00; B01D 15/10; B05D 1/36
See application file for complete search history.

COUPLING OF THIN LAYER CHROMATOGRAPHY (TLC) TO QUANTUM CASCADE LASER SPECTROSCOPY (QCLS) FOR QUALITATIVE AND QUANTITATIVE FIELD ANALYSES OF EXPLOSIVES AND OTHER POLLUTANTS

BACKGROUND OF THE INVENTION

There is an urgent need for instrumentation that is capable of sustaining the development of rapid methods for the isolation, detection, and identification of traces of chemical and biological threat agents present in complex media. From anti-terrorist personnel, to first responders and law enforcement employees, police officers, airport screeners, and border patrol personnel, as well as members of the Navy, Army, Air Force, and National Guard, the risk of coming into contact with explosives and other weapons of mass destruction is high. Many of the samples collected for the forensic detection of explosives come from complex matrices that contain soil, dirt and other interfering substances. Additionally, soils can be contaminated with explosives by a number of different human activities, such as the use of explosives on training ranges, sites for the synthesis of explosives, as a result of conflicts between nations, from used waters and wastes in clandestine laboratories, and as a result of terrorist events, among others. Other common substrates that can be targets for the detection of explosives include debris, metals, plastics, woods, cardboard, fabrics, and so forth.

The majority of studies that have been published regarding the detection of explosives are based on spectroscopic and chromatographic methodologies, which obtain very low limits of detection. However, the use of chromatographic techniques in field applications has been very limited, primarily because of the lack of portable instrumentation. Conversely, many spectroscopic techniques have been successfully tested in field applications, facilitating the rapid acquisition of data and information, thereby leading to prompt decisions based on the obtained results and thus saving numerous lives and reducing casualties. Vibrational spectroscopy has been demonstrated to be valuable for the detection of high explosives, homemade explosives and toxic industrial compounds. In particular, infrared spectroscopy (IRS) has played a unique role in the detection of threat compounds. This technique has also been used for the post-blast detection of energetic materials using both globar and synchrotron infrared radiation sources, thus validating Fourier transform infrared (FT-IR) spectroscopy as a useful tool for forensic applications. The MIR spectral region consists of the spectral window from approximately 350 to 4000 $cm^{-1}$. In this range, all molecules have characteristic vibrational signals that can be excited upon interaction with photons from the excitation source, thereby enabling the detection of trace amounts of compounds.

Thin layer chromatography (TLC) provides a streamlined sampling and testing protocol that allows for the rapid and reproducible separation of drugs, explosives and precursors, and pollutants, and its use can be extended to a wide range of hazardous materials obtained from substrates, liquids and solids for laboratory and field operations. The use of IRS as a detection/identification technique arises from the need to reliably identify the components separated by TLC. IRS has a high discrimination capability, and therefore, it is in principle a powerful identification method. Provided that reference spectra are available, almost all analytes, including structural isomers, can be nearly unambiguously identified based on their IR spectrum. Thus, the technique changes from a presumptive analysis (when TLC is used alone) to a confirmatory analysis when the separation technique is coupled with IRS. When reference spectra are unavailable, valuable information about the molecular structures of the analyzed compounds may still be obtained by spectral interpretation.

The majority of studies that have been published on the detection of explosives are based on spectroscopic and chromatographic methodologies, which obtain very low limits of detection. However, the use of chromatographic techniques in field applications has been very limited, primarily because of the lack of portable instrumentation. Conversely, spectroscopic techniques have the advantage of being tested in field applications, facilitating the rapid acquisition of data and information, thereby leading to prompt decisions based on the obtained results and thus saving numerous lives and reducing casualties. Vibrational spectroscopy has been demonstrated to be valuable for the detection of high explosives, homemade explosives and toxic industrial compounds. In particular, infrared spectroscopy (IRS) has played a unique role in the detection of threat compounds and has been used for the post-blast detection of energetic materials using both globar and synchrotron infrared radiation sources, thereby validating FT-IR spectroscopy as a useful tool for forensic applications. The MIR spectral region consists of the spectral window from approximately 350 to 4000 $cm^{-1}$. In this range, all molecules have characteristic vibrational signals that can be excited upon interaction with photons from the excitation source, enabling the detection of trace amounts of compounds. TLC provides a streamlined sampling and testing protocol that allows for the rapid and reproducible separation and identification of drugs, explosives, and precursors, and its use has been extended to a wide range of hazardous materials obtained from surfaces, liquids and solids in laboratory and field operations. The use of IRS as a detection/identification technique arises from the need to reliably identify the components separated by TLC. IRS has a high discrimination capability and is therefore in principle a powerful identification method. If reference spectra are available, almost all analytes, including structural isomers, can nearly be unambiguously identified based on their IR spectrum. Thus, the TLC-IRS technique changes from a presumptive analysis (when TLC is used alone) to a confirmatory analysis when coupled with IRS. Valuable information about the molecular structures of the analyzed compounds may still be obtained by spectral interpretation when reference spectra are not available.

The first in situ FT-IR detection of spots on a plate was demonstrated by Percival and Griffiths. A thin layer (depth: 100 μm) of adsorbent on an IR transparent support (AgCl) allowed IR transmission measurements of dyes and amino acids at the 1-10 μg levels. In 1978, Fuller and Griffiths demonstrated the viability of diffuse reflectance IRS (DRIRS) in measurements of methylene blue on a silica plate. Since then, DRIRS has become the most commonly used method for performing in situ TLC detection with FT-IR. Several studies have been performed to explore the potential of TLC-DRIRS analysis. These studies, which have been extensively reviewed by Brown and Beauchemin, revealed that various conventional TLC phases, such as silica, alumina, cellulose and reversed-phase materials, can be used in combination with DRIRS to provide minimum identifiable quantities (identification limits) down to approximately 1 μg. The main difficulty encountered when using DRIRS as an in situ detection method for TLC is the strong absorption background of the adsorbent material, which causes serious interferences in particular spectral regions. For example, silica gel absorbs strongly in the regions from 3100 to 3700 cm$^{-1}$ and from 1600 to 800 cm$^{-1}$, obscuring possible analyte vibrational signals at these frequencies. Consequently, the DRIRS spectrum of a TLC spot is divided into main parts: spectral areas where the sensitivity is high and that are appropriate for obtaining analyte information and spectral regions where the signal-to-noise ratio is poor and only minimal information can be extracted.

The development of more powerful IR sources gave rise to collimated, coherent, and polarized sources. These sources were first developed at Bell Labs in 1994 with the invention of quantum cascade lasers (QCLs). QCLs are a commercially available and portable setup allowing the detection of chemical and biological threat compounds in the field, such as explosives including TATP, PENT, RDX, and TNT. Coupling with chromatographic techniques, such as TLC with QCL spectroscopy, for detecting explosives (or any chemical compound) has not been previously reported. The possibility of detecting explosives in the field more than justifies the coupling of TLC with QCL spectroscopy (QCLS).

TLC-QCLS, as a portable coupled technique for the analysis of explosives, will be most commonly used in two situations: (1) post-blast examination and (2) identification of suspected explosive materials (pre-blast analyses on bulk material). In a post-blast situation, preliminary results can lend support to the link between multiple incidents or between a terrorist incident and the organization potentially responsible for the incident. This portable coupled technique can provide critical information for the identification of a suspected explosive material. In these situations, portable instrumentation has a two-fold advantage: (1) the speed with which results can be obtained, and (2) eliminating the need to transport potentially dangerous materials to a laboratory. Identification at a scene enables informed decisions to be made concerning render-safe procedures and the transportation of materials. This is of particular importance when extremely sensitive explosives, such as organic peroxides, are suspected. When portable instruments are utilized during searches authorized by search warrants, the preliminary results can be used to indicate areas where more efforts should be directed. The preliminary results can also provide advanced warning about which types of explosives may be encountered at a scene and hence enable searchers to be better informed of the safety risks at a particular scene.

In this invention, a methodology that allows for the detection of explosives, such as TNT, present in real world samples (i.e., soils) and in complex substrates using TLC-QCLS is demonstrated. The tested methodology enabled the rapid and reproducible separation and identification of targeted explosives at near trace levels (~ng) in the field in a short amount of time. The results show that TLC-QCLS, as a coupled technique, is an excellent approach to use in the lab or in chemical analyses in the field.

BRIEF DESCRIPTION OF THE DRAWINGS

The patent of application file contains at least one drawing executed in color. Copies of this patent or patent application publication with color drawing(s) will be provided by the Office upon request and payment of the necessary fee.

Further features and advantages of the invention will become apparent from the following detailed description taken in conjunction with the accompanying figures showing illustrative embodiments of the invention, in which.

Figure 1:
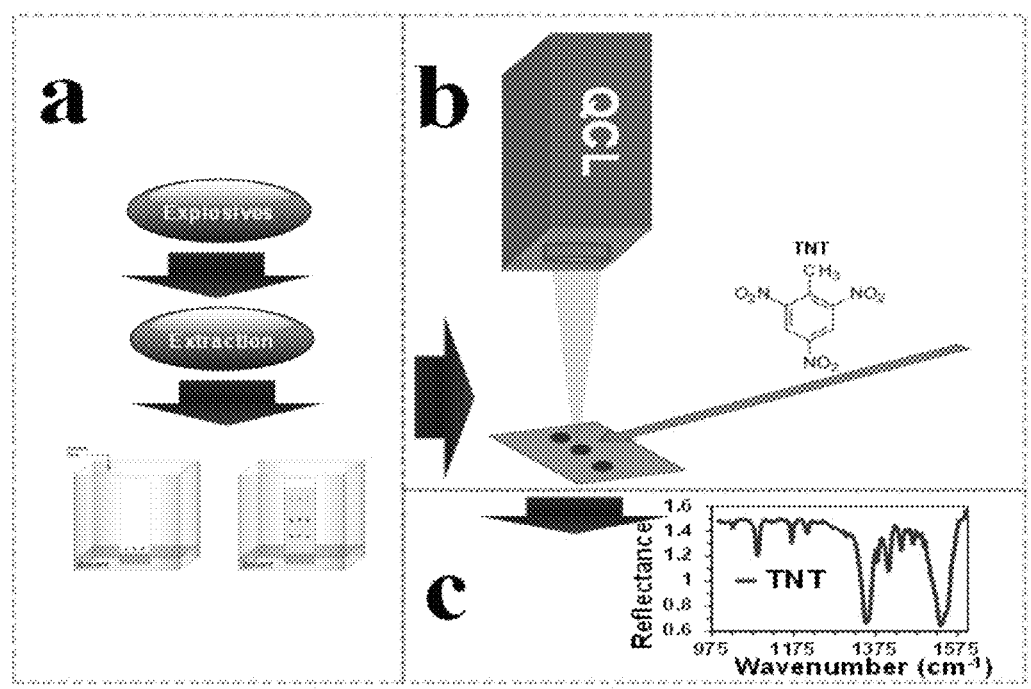
FIG. 1 shows the experimental setup of the system, according to the present invention.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

The present invention is related to the use of instrumentation to develop methods for the rapid separation, detection, and identification of chemical compounds by coupling a well-established chromatographic separation science technique, TLC, with mid-infrared (MIR) QCLS for the analysis of explosives, pollutants, and other threat chemicals. In this invention, the stationary phases were silica gel adhered to metallic aluminum supports. The mobile phases consisted of organic solvents and their mixes. In the proof-of-concept chromatographic separations, the retention factors ($R_f$) for TNT were determined for several solvents and solvent mixtures. The position and spot diameter of the TNT samples on the plate containing the adsorbent silica film were measured and compared before and after the chromatographic runs. The best mobile phase for separating TNT ($R_f$=0.75±0.01) was the solvent mixture of hexane:toluene in the proportion of 1:4. In most cases, the change in the size of the spot diameters before and after the chromatographic runs was approximately 0.5 cm. The MIR vibrational identification of TNT was performed through reflectance measurements using a widely tunable three-diode source. The symmetric stretching vibration of the nitro group [$v_s(NO_2)$] centered at approximately 1350 cm$^{-1}$ and the asymmetric stretching vibration of the nitro group [$v_{as}(NO_2)$] at approximately 1530 cm$^{-1}$ were clearly observed. The results obtained in numerous tests demonstrated that TLC-QCLS allows for the rapid and reproducible separation, identification, and quantification of explosives in the field in a short amount of time. This coupled technique is attractive for defense and security applications.

Sample Preparation: TLC

The developing chamber for TLC was a jar with a lid, with dimensions of 5 cm wide×10 cm tall, to which a sample of 5 mL of the solvent (or mixture of solvents) was added to a depth of just less than 0.5 cm. The jar was allowed to stand to saturate the TLC chamber with solvent vapors while the aluminum-supported silica gel TLC plates (Merck, TLC Silica gel 60 F254) were prepared. The TLC plates used were cut to a convenient size of 2 cm wide×9 cm tall and were carefully handled to avoid damage or contamination of the adsorbent layer. Then, a line was drawn across the TLC plate 1.5 cm from the bottom using a graphite lead pencil. Subsequently, 10 µL of the explosive material dissolved in methanol was placed at the center of the marked line by gently touching the TLC plate, and then the methanol was allowed to evaporate. The prepared TLC plate was placed in the developing chamber and covered. The TLC plate was allowed to develop until the solvent was approximately 0.5 cm centimeters below the top of the plate. Then, the plate was immediately removed from the developing chamber, and the solvent front was marked using a graphite pencil and allowed dry. If there were any colored spots, they were marked lightly using a graphite pencil by tracing circles around the spots. If the spots corresponding to separated analytes did not exhibit color (such as in the case for target explosives), they were visualized using a UV lamp ($\lambda$=254 nm) and then marked with circles. The distances traveled by the solvent and the explosive materials (spots) were measured, and the $R_f$ values were calculated as the ratio of the distance traveled by the solvent+analyte (spot) divided by the distance traveled by the neat solvent. If no luminescence was observed when using the UV lamp, then a chromogenic reagent consisting of an aerosol containing 1% diphenylamine (DPA) in methanol was sprayed to chemically develop the analyte spots. In this case, TNT and PETN exhibited orange and gray-green colors, respectively. The spot diameters of the sample on the silica plate before and after the chromatographic run were measured and compared.

Experimental Setup

Solutions of explosives containing from 0.39 µg to 100 µg of explosive were transferred as previously discussed using micropipettes to perform their respective chromatographic runs. Spots were identified using the UV lamp. Finally, each spot was examined using QCLS to obtain their diffuse reflectance MIR spectra and to identify their characteristic vibrational signatures. FIG. 1 shows the experimental setup used. The experimental details of the setup used in this invention are as follows: (a) sample preparation, extraction, and chromatographic separation from matrices; (b) in situ QCLS spectral measurements; and (c) analysis of spectroscopic signatures. Taking into consideration the setup illustrated in FIG. 1, area b, the configuration used to record vibrational spectra was operated in transflectance mode because the matrix that contains the samples (separated explosives) is a dielectric material with lower reflectivity than metals.

TLC: TNT

Various organic solvents were used as mobile phases to separate the two nitroexplosives used as a proof of concept: TNT and PETN. Among the solvents used were toluene, methanol, hexane, acetone, ethyl acetate, dichloromethane, ether, and their binary mixtures in various proportions. The best mobile phase for separating TNT ($R_f$=0.56±0.01) and PETN ($R_f$=0.45±0.01) was the mixture hexane:toluene (1:4). Other solvent systems also worked well, but the obtained $R_f$ values were either low or too high. This led to the selection of hexane:toluene (1:4) because this solvent combination had mid $R_f$ values that could separate the target from possible interfering contaminants. The spot diameters of the sample on the silica plate before and after the chromatographic run were, on average, 4±1 mm and 6±1 mm, respectively. The time for chromatographic development was ~10±1 min.

Figure 2:
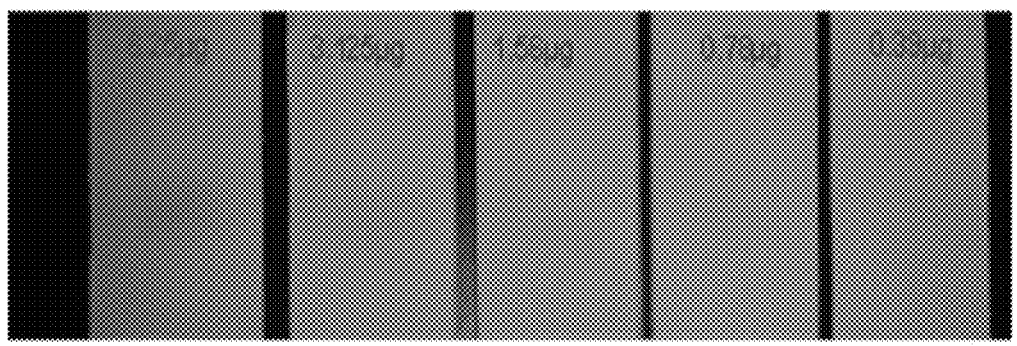
FIG. 2 shows an image of TNT spots on silica gel TLC in at various analyte concentrations, according to the present invention.

FIG. 2 shows the spots for TNT at different concentrations (0.39-6.25 µg/spot) using DPA reagent to generate a characteristic orange color corresponding to TNT. Note that it was not possible to visually detect the presence of any nitroexplosive present at analyte concentrations lower than 1.56 µg/spot. This result justifies the need to couple TLC with a technique capable of providing characteristic vibrational information of the analyte, such as QCLS. Note that when infrared spectra were recorded, no DPA reagent was added. DPA was only initially used to calculate the $R_f$ values and spot diameters before and after chromatographic runs.

Spectral Profiles of High Explosives TNT

Figure 3:
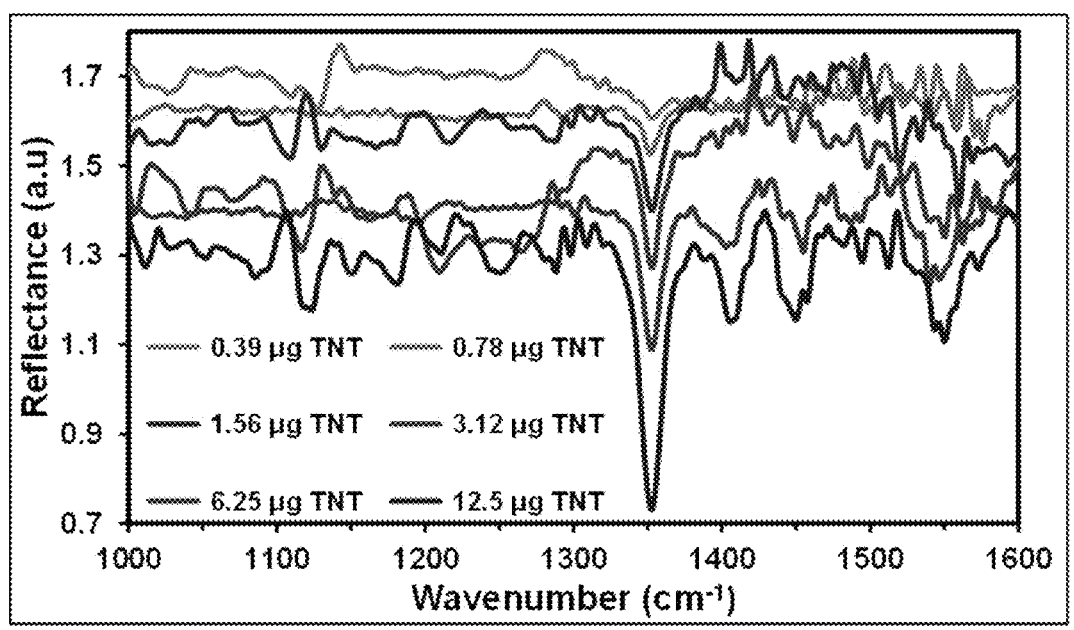
FIG. 3 shows TNT spectra on silica gel-TLC for several concentrations of the nitroaromatic high explosive, according to the present invention.

TNT was chosen as model to evaluate the ability for identification of the vibrational signals of nitroexplosives on silica gel TLC plates using QCLS. QCL diffuse reflectance spectra of TNT on silica gel media are illustrated in FIG. 3. The spectral range covered by the three-diode laser system was 1000-1600 cm$^{-1}$. The characteristic bands of TNT can be clearly observed. These IR spectra were acquired in situ, using a TLC portion free of any chemical interferences as background. Some of the vibrational bands that were tentatively assigned to TNT (see for example the strong blue trace spectrum corresponding to 12.5 µg in FIG. 3) were: 1024 cm$^{-1}$ (CH$_3$— deformation), 1086 cm$^{-1}$ (C—H ring in-plane bending), 1350 cm$^{-1}$ (symmetric stretching of nitro groups) and 1551 cm$^{-1}$ (asymmetric NO$_2$ stretching).

As can be observed in FIG. 3, as the concentration decreases, the intensity of the IR vibrational bands decreases. At the same time MIR bands (~1550 cm$^{-1}$) disappear at concentrations lower than about 3.12 µg. This may be due to the effect of the presence of the ro-vibrational bands of water vapor starting at ca. 1400 cm$^{-1}$ and to the strong abortion bands of silica gel in the region of 1400-1600 cm$^{-1}$. However, the MIR band about 1350 cm$^{-1}$, characteristic of nitro group's vibrations is noticeable even at very low TNT amounts allowing obtaining molecular information from target nitroexplosive at 390 ng. The spectra shown in FIG. 3 demonstrate that hyphenated technique TLC-QCLS can be applied successfully for the identification and quantification of explosive seven at semi-trace levels.

Figure 4:
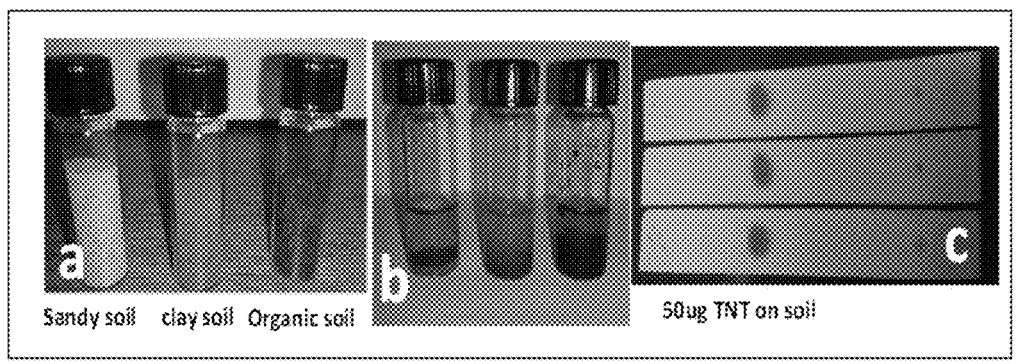
FIG. 4 shows images of TLC-QCLS experiments for detection of TNT in soils, according to the present invention.
Figure 5:
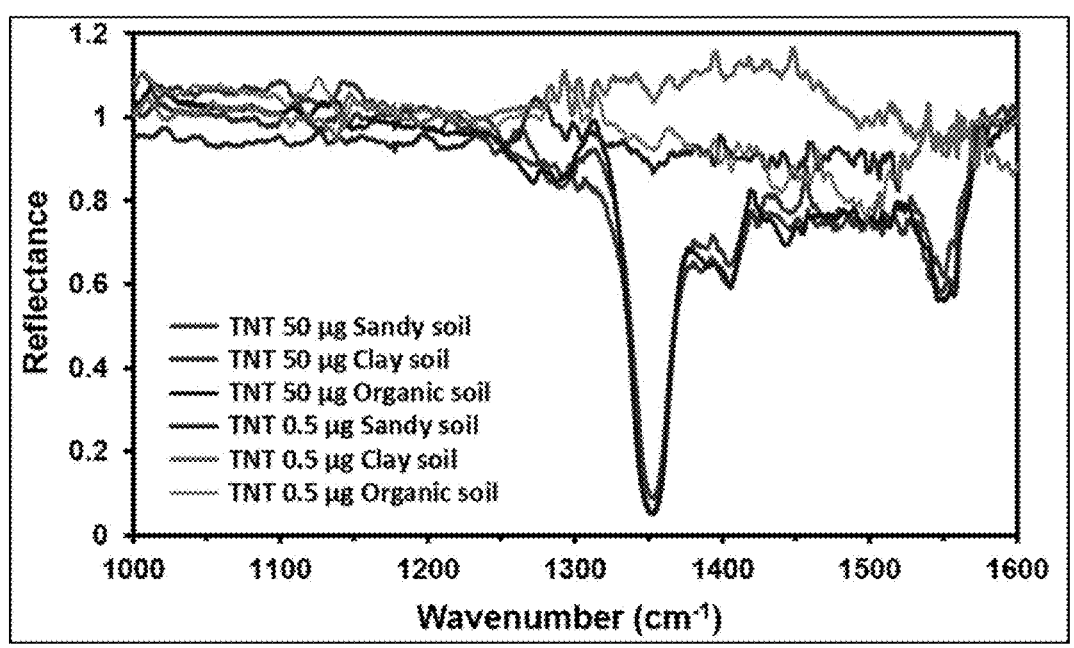
FIG. 5 shows TLC-QCLS spectra of extracted TNT samples from various soil types, according to the present invention.

To evaluate TLC-QCLS in the detection of explosives present in complex matrices, soil samples contaminated with TNT were prepared as follows: 0.5 g of dry soil were placed in a glass vial (7 mL, capacity) covered with screw top and 2 mL solution of TNT in methanol were added (see FIG. 4, image a). Then the vial was mixed by stirring manually for 2 min and finally left standing for 5 min (see FIG. 4, image b). Solvent was allowed to evaporate, while the explosive was adsorbed by the soil matrix. Then 2 mL of the hexane:toluene (1:4) solvent mix were added to the soil samples containing TNT as contaminant to extract the target explosive. Next, the supernatant solution was sampled by removing 10 µL aliquots containing ~50 µg or ~0.5 µg TNT and were deposited on silica gel TLC plates. The solvent was allowed to evaporate and the TLC plates were placed in the developing chambers to perform the chromatographic runs as described before. Spot visualization was carried out using a UV lamp (see FIG. 4, image c), although this was not necessary since the $R_f$=0.56±0.01 was deemed very reproducible. Then the MIR vibrational detection on the spots was performed using QCLS. In this test sandy, clay, and organic soils were used. FIG. 5 shows TNT QCL spectra from the three different soil types at ~50 and ~0.5 µg/spot.

The spectra shown in FIG. 5 demonstrate that TLC-QCLS can serve as an excellent platform to devise analytical methods useful for separation, identification, and quantification of chemical targets. QCL spectra of TLC runs of TNT in contact with soil samples, at various mass levels (0.5 to 50 µg/spot) were very similar to the TNT reference spectra obtained from the literature and to the QCL reflectance spectra of neat TNT (FIG. 3). TNT prominent MIR band at about 1350 cm$^{-1}$ can be clearly observed even at low amounts as 500 ng/spot.

Although the present invention has been described herein with reference to the foregoing exemplary embodiment, this embodiment does not serve to limit the scope of the present invention. Accordingly, those skilled in the art to which the present invention pertains will appreciate that various modifications and equivalents are possible, without departing from the technical spirit of the present invention.

The invention claimed is:

1. A method for detecting the presence of a target material on a sample, the method comprising:
    performing thin-layer chromatography to a sample placed on a plate of a stationary phase in order to separate every analyte present on said sample into a corresponding spot on the plate;
    performing Quantum Cascade Laser spectroscopy on said sample to obtain diffuse reflectance spectra from each spot on said plate; and
    identifying from said diffuse reflectance spectra a spectral profile of a target material.

2. The method of claim 1, wherein said target material is a nitroexplosive material.

3. The method of claim 1, wherein said target material comprises at least one of: trinitrotoluene, triacetone triperoxide, cyclonite (RDX) and pentaerythritol tetranitrate (PSTN).

4. The method of claim 1, wherein a mobile phase of said thin-layer chromatography comprises at least one solvent.

5. The method of claim 1, wherein a mobile phase of said thin-layer chromatography comprises a mixture of hexane and toluene.

6. The method of claim 5, wherein hexane and toluene are provided in a proportion of 1:4.

7. The method of claim 1, wherein said diffuse reflectance spectra is obtained by quantum cascade laser spectroscopy.

8. The method of claim 1, wherein said Quantum Cascade Laser spectroscopy is performed on a mid-infrared region.

9. The method of claim 1, wherein said spectral profile comprises a vibrational signature of the target material.

10. The method of claim 1, further quantifying a concentration of said target material from said diffuse reflectance spectra.

* * * * *